US005115809A

United States Patent [19]

Saitoh et al.

[11] Patent Number: 5,115,809

[45] Date of Patent: May 26, 1992

[54] ULTRASONIC PROBE

[75] Inventors: Shiroh Saitoh, Yokohama; Mamoru Izumi, Tokyo; Syuzi Suzuki; Shinichi Hashimoto, both of Yokohama, all of Japan

[73] Assignee: Kabushiki Kaisha Toshiba, Kawasaki, Japan

[21] Appl. No.: 500,945

[22] Filed: Mar. 29, 1990

[30] Foreign Application Priority Data

Mar. 31, 1989 [JP] Japan .................................. 1-83704

[51] Int. Cl.[5] .............................................. A61B 8/14

[52] U.S. Cl. ................................................ 128/662.03

[58] Field of Search ....................... 128/662.03, 660.01, 128/662.04, 662.05, 662.06, 663.01

[56] References Cited

FOREIGN PATENT DOCUMENTS 2949991 7/1981 Fed. Rep. of Germany .
8523024 3/1987 Fed. Rep. of Germany .
3729731 4/1988 Fed. Rep. of Germany .
3805268 9/1988 Fed. Rep. of Germany .
61-69299 4/1986 Japan .
61-69300 4/1986 Japan .

OTHER PUBLICATIONS

IEEE Transactions on Ultrasonics, Ferroelectrics and Frequency Control, vol. 36, No. 6, Nov. 1989; "Apodization of Multilayer Bulk Wave Transducers", E. Akcakaya et al; 1989.

*Primary Examiner*—William E. Kamm
*Assistant Examiner*—Kevin Pontius
*Attorney, Agent, or Firm*—Oblon, Spivak, McClelland, Maier & Neustadt

[57] ABSTRACT

An ultrasonic probe includes a probe head having a piezoelectric element which includes a plurality of piezoelectric layers which are laminated in the thickness direction thereof with the polarity directions of the adjacent piezoelectric layers set opposite to each other and each of which has opposite end surfaces, electrodes formed on the opposite end surfaces of the piezoelectric layers in the laminated direction, a plurality of external electrodes formed on the opposite end surfaces of the piezoelectric layers on the laminated direction, internal electrodes formed in the lamination interface of the piezoelectric layers, an acoustic matching layer having a plurality of layers and formed on one surface of the plurality of laminated piezoelectric layers, an acoustic lens disposed on the matching layer with the convex surface thereof set towards the outside, and a backing material disposed on the other surface of the piezoelectric element.

11 Claims, 4 Drawing Sheets

ULTRASONIC PROBE

BACKGROUND OF THE INVENTION

1. Field of the Invention

This invention relates to an ultrasonic probe used in an ultrasonic imaging device or the like, and more particularly to an ultrasonic probe constituted by a multilayer piezoelectric material.

2. Description of the Related Art

The following patent disclosures which explain the related art can be given:

(1) Japanese Patent Disclosure (Koukai) No. 60-41399; and (2) Japanese Patent Disclosure (Koukai) No. 61-69298.

The ultrasonic probe is constructed mainly by a piezoelectric element which is used to obtain image data indicating the internal state of an object by receiving ultrasonic waves reflected from the interface in the object having a different acoustic impedance when ultrasonic waves are applied to the object. For example, an ultrasonic diagnostic apparatus for examining the internal portion of a human body and an inspecting apparatus for searching for scars occurring in the internal portion of welded metal may be given as concrete examples of the ultrasonic.imaging apparatus using the above ultrasonic probe.

In the ultrasonic diagnostic apparatus, it is required to obtain high-resolution images with a high sensitivity so that a cavity (gap) which is caused by the small physical variation due to variation in the condition of a patient can be clearly observed. It is considered to increase the number of elements of a transducer or raising the resonant frequency thereof as a method for attaining the high-resolution required for the ultrasonic probe.

In a case where the number of elements of the transducer used in the ultrasonic probe is increased to attain the above purpose, the resolution in a direction parallel to the array of the transducer elements can be enhanced. At the same time, the ultrasonic wave radiation area for each transducer element is reduced and the impedance of each transducer element is increased. In particular, the ultrasonic wave radiation area of each transducer element in an electronic sector scanning probe for effecting the sector-scanning operation by supplying driving signals to a plurality of strip-form transducer elements with a time delay may be reduced to ½ to 1/5 of that obtained in a linear scanning probe having the same construction and effecting the linear scanning operation, and therefore, the impedance of each transducer element is increased more significantly. As a result, the voltage loss caused in the sector scanning probe by the presence of the electrostatic capacitance of a coaxial cable connecting the probe head to the main section of the device becomes larger in comparison with that of the linear scanning probe.

In a case where the resonant frequency used in the ultrasonic probe is increased to attain the above purpose, it must be considered that, in recent years, it has been required to observe intraepidermal tissue or internal body tissue of a patient under operation as an image with a high resolution. In order to meet the requirements, the frequency is set in the range of 15 to 30 MHz. However, since the ultrasonic probe generally utilizes the thickness expander mode of the piezoelectric element, it is necessary to make the piezoelectric element thin in order to attain the high frequency operation. This problem becomes more severe in ultrasonic probes using a multilayer piezoelectric material disclosed in Japanese Patent Disclosure No. 61-69298, for example. That is, in the multilayer piezoelectric material disclosed in the above Japanese Patent Disclosure, since piezoelectric layers are electrically connected in parallel, a resonance occurs at a frequency of the ultrasonic wave set when the total thickness of the multilayer piezoelectric material (total thickness of a plurality of laminated piezo electrodes) becomes equal to half the wavelength thereof. Therefore, in electric material must be formed as thin as possible.

In general the piezoelectric element may be roughly divided into two types; piezoelectric ceramic and high-polymer piezoelectric element.

In the case of piezoelectric ceramic, the thickness of the piezoelectric element is less than 100 $\mu m$. In the extremely thin piezoelectric element, and particularly, in the case of using ceramic such as PZT-series ceramic containing lead, the characteristic of the ceramic is largely influenced by lead diffused into the sintering atmosphere in the sintering process. As a result, the characteristic of the ceramic is degraded, the piezoelectric element itself may be warped, and at the same time, the workability thereof becomes lowered. Further, in most of the ordinary piezoelectric elements, sintered electrodes of silver or the like are bonded thereto, and in this case, printing electrode paste containing glass frit for closely joining silver and ceramic is used so that the ratio of the glass frit diffused into the ceramic may increase with a decrease in the thickness of the ceramic. As a result, the characteristic of the piezoelectric element itself may be degraded.

In the case of high-polymer piezoelectric element, the piezoelectric element is soft in comparison with the piezoelectric ceramic and may be less damaged. However, it has the following defects. That is, the electromechanical coupling factor thereof is as small as 0.2 to 0.3. The dielectric constant thereof is smaller by more than two digits in comparison with that of ceramic. The glass transition temperature thereof is as low as approx. 100° C. Therefore, the high-polymer piezoelectric element is not generally used as an array probe.

As described above, the two types of piezoelectric elements have defects from the view points of material, shape and the like.

The following three methods for obtaining images at a high sensitivity by use of the ultrasonic probe are given:

(1) increase the electromechanical coupling factor of the piezoelectric element;

(2) obtain the acoustic matching; and (3) obtain the electrical matching.

The maximum value of $k'_{33}$ of the currently available piezoelectric ceramic material which can be used to effect the above method (1) is approx. 0.7. Much effort has been made to increase the electromechanical coupling factor, but optimum material as the piezoelectric element better than lead zirconate titanate-series ceramic represented as PZT developed by Clevite Co. in 1955 has not been developed.

In order to effect the method (2), the difference of the acoustic impedance between the piezoelectric element and the living body becomes large and therefore a method for forming an acoustic matching layer is used. The number of acoustic matching layers may be set to one, or more than one, but the improvement over the piezoelectric element currently used cannot be expected only by using the acoustic matching layer.

Various methods are used to effect the method (3). In the ultrasonic diagnostic apparatus, the number of elements of the ultrasonic probe tends to increase because of the high-resolution required in recent years. Therefore, the ultrasonic wave radiation area for each element becomes small and the impedance thereof becomes large. As a result, the voltage loss due to the presence of the electrostatic capacitance of the coaxial cable becomes larger as described before.

Further, the electronic sector scanning probe is not only used in the operation of photographing B mode images which are the tomographic images of the living body, but also often used in the photographing operation in the Doppler mode in which the blood flow rate in the heart, liver, carotid artery or the like is displayed in color by making use of the Doppler shift (Doppler effect) of the ultrasonic waves caused by the blood flow therein. In the case of the Doppler mode, since the reflected echo from fine corpuscles with the diameter of several μm is used, the level of a signal obtained is low in comparison with the case of the above-described B mode. Therefore, the sensitivity margin in the Doppler mode is small in comparison with the case of the B mode and it is necessary to further enhance the sensitivity.

Recently, a "color flow mapping (CFM) method" for two-dimensionally mapping the diffusion of blood flow on the real time base and color-displaying the flow and reflection power of the blood flow is widely used, and therefore the diagnostic function and the diagnostic application field are significantly enlarged. The CFM method is used for the diagnostic of various organs of a human body such as the uterus, kidney and pancreas. Now, the research and development of the diagnostic apparatus for making it possible to observe the movement of coronary blood flow are made in various hospitals and research laboratories.

It will be understood difficult from consideration of the inherent property of the probe to observe the weak blood flow such as coronary blood flow and variation in the blood flow caused by hyperplasia of early cancerous cells. In order to solve the above problem, probe heads which are improved to reduce the loss caused by the electrostatic capacitance of the coaxial cable by inserting an emitter follower circuit used as an impedance transducer between the probe head and the coaxial cable are practically used. However, even with this type of probe, it is difficult to observe the weak blood flow described before.

When the improvement of an ultrasonic diagnostic apparatus is considered, it is possible to enhance the sensitivity thereof by raising the driving voltage supplied to the probe head. However, since the electric power supplied to the piezoelectric element is also increased, heat caused by the dielectric loss and ultrasonic power irradiated to acoustic lens or backing material may be generated and the generated heat may degrade the characteristic of the probe or give damage such as a burn to the human body. Therefore, increase in the driving voltage is limited, and the sensitivity cannot be sufficiently enhanced only by the improvement made by the above method.

In addition to the improvement made by the above method, the following improvements are further developed. In general, the reference frequency in the Doppler mode is set lower than the center frequency of the frequency bandwidth of the ultrasonic probe. The reason for this is that it is preferable to us low frequency ultrasonic waves in order to suppress the influence by reduction in the S/N ratio due to attenuation of the ultrasonic waves in the living body. Therefore, if ultrasonic waves having two types of frequency components can be transmitted/received by a single ultrasonic probe, it becomes possible to obtain the B mode image of high resolution in the high frequency components and the Doppler image of high sensitivity in the low frequency components. In order to realize such a device, "duplex type ultrasonic probes" in each of which two types of transducers having different resonant frequencies are provided in a single ultrasonic probe head are manufactured and sold from various makers. However, since this type of ultrasonic probe has a plurality of transducers having different resonant frequencies, the ultrasonic wave transmission and reception planes are set in different positions, making it impossible to observe the same tomographic image.

Therefore there is proposed a device which can transmit/receive ultrasonic waves having two different types of frequency bands by means of a single transducer and which is formed by using a multilayer piezoelectric material constructed as is disclosed in Japanese Patent Disclosure No. 60-41399. That is, the two types of frequency bandwidths can be separated by use of a combination of the ultrasonic probe, a driving pulse width and a filter, and as a result, the B mode signal and Doppler signal can be separately obtained by use of the high-frequency components and low-frequency components, respectively. However, even with the ultrasonic probe of the above construction, since the electromechanical coupling factor of a single piezoelectric element is substantially equally divided, the frequency band on the high-frequency side becomes narrow and the tailing remaining of the echo signal is lengthened. As a result, the high resolution cannot be enhanced to an expected value even when attempt is made to obtain a B mode image of high resolution by the high frequency components. Further, since the low frequency components tend to be reduced as the frequency band becomes narrower, the S/N ratio thereof is lowered, thus causing insufficient penetration. The reason is that the frequency component of an echo signal from the deep portion of the living body is constituted by components of frequencies lower than the center frequency of the transmitted ultrasonic waves. The specific frequency bandwidth required for obtaining preferable B mode images is more than 40% of the center frequency. For example, the specific bandwidth at −6 dB is 40 to 50% in the case of a single-layered matching and 60 to 70% in the case of two-layered matching when a piezoelectric element of single layer structure is used. In contrast, when the piezoelectric element of the above construction is used, the specific bandwidth is 25% of the center frequency in the case of a single-layered matching and 35% in the case of two-layered matching. Thus, the specific bandwidth which is only half that obtained when the conventional single-layered piezoelectric element is used can be obtained, and therefore further improvement must be made in this respect.

As described above, when the piezoelectric ceramic is used in the conventional technology for setting the frequency high by reducing the thickness of the piezoelectric element so as to attain an ultrasonic probe of high resolution, the thickness must be made extremely thin. Therefore, problems occur from the view points of manufacturing method and characteristic thereof. Further, the high-polymer piezoelectric element cannot be practically used because of the small electrode mechanical coupling factor thereof.

In the electronic sector scanning probe often used in the Doppler mode, it cannot be expected to significantly enhance the sensitivity by properly selecting the material of the piezoelectric element and disposing an acoustic matching layer. It is pointed out that the sensitivity is not so high even in the probe head in which the voltage loss caused by the electrostatic capacitance of the cable itself is reduced by inserting the emitter follower circuit between the probe and the coaxial cable.

Further, the method for enhancing the sensitivity by raising the driving voltage is restricted by the problem of heat generation in the piezoelectric element. Also, in a case where two different frequency bandwidths are obtained by using a single ultrasonic probe, there is provided a problem that the same portion cannot be observed when a plurality of transducers having different resonant frequencies are used. Further, a multilayer piezoelectric material which is proposed to solve the above problem and is formed by laminating piezoelectric elements having substantially the same thickness as the single-layered piezoelectric element disclosed in Japanese Patent Disclosure No. 60-41399 has a problem that the specific frequency bandwidth of the high-frequency components is narrow.

SUMMARY OF THE INVENTION

An object of this invention is to provide an ultrasonic probe which can easily attain the high-frequency operation without causing problems on the manufacturing process and the characteristic.

Another object of this invention is to provide an ultrasonic probe which can attain the high-frequency operation and high sensitivity and transmit/receive two different ultrasonic waves on the same plane of the probe head and in which the high-frequency components have a sufficiently wide bandwidth.

The probe head of the ultrasonic probe according to this invention is designed as follows.

It is constituted by a multilayer piezoelectric material having a plurality of piezoelectric layers with the polarized directions of the adjacent piezoelectric layers set opposite to each other and electrodes formed on the opposite end surfaces thereof in the laminated direction.

In a case where the ultrasonic probe is used for the ultrasonic diagnostic apparatus, an impedance transducer is inserted between the multilayer piezoelectric material and the coaxial cable.

Further, there is provided an ultrasonic probe using the multilayer piezoelectric material in which the thickness of a piezoelectric layer adjacent to a substrate (backing material) or the end face opposite to the ultrasonic wave radiation plane formed on one surface of the laminated piezoelectric layers in the thickness direction is set to be smaller than that of the other piezoelectric layer.

The multilayer piezoelectric material of this invention is formed of a plurality of piezoelectric layers electrically connected in series and laminated with the polarized directions of the adjacent piezoelectric layers set opposite to each other, and the basic resonance frequency thereof does not depend on the total thickness thereof unlike the conventional multilayer piezoelectric material having a single piezoelectric element or a plurality of piezo electrodes electrically connected in parallel, and is set to a frequency determined by the thickness of the individual piezoelectric layers. Therefore, if the number of laminated piezoelectric layers is set to n, the multilayer piezoelectric material may have a thickness equal to n times the thickness of the single-layered piezoelectric element and has the same resonant frequency as the single-layered piezoelectric element. For the above reason, the high-frequency operation of the ultrasonic probe can be easily attained without reducing the total thickness of the piezoelectric element, that is, without causing any problem on the manufacturing process and the characteristic thereof.

Further, the multilayer piezoelectric material having a plurality of piezoelectric layers electrically connected in series as described above generally has an increased impedance and therefore the voltage loss causing degradation i the sensitivity due to the presence of the electrostatic capacitance of the coaxial cable can be reduced by inserting an impedance transducer between the probe head and the coaxial cable to lower the impedance. In addition, ultrasonic waves, particularly second or succeeding ultrasonic waves radiated from one plane of the multilayer piezoelectric material of this invention is combined with waves propagated from the other plane of the multilayer piezoelectric material and the waves reflected at the both planes thereof. In this case, since total thickness of the multilayer piezoelectric material is larger than that of the single-layered multilayer piezoelectric material, the number of reflections at the end plane becomes less than in the case of the single-layered multilayer piezoelectric material and accordingly the amplitude of the ultrasonic waves becomes larger. When the ultrasonic waves, particularly second and succeeding ultrasonic waves in the multilayer piezoelectric material of this invention becomes larger. Therefore, the sensitivity of the ultrasonic probe can be easily enhanced.

Further, the multilayer piezoelectric material of this invention has one end surface which is formed of the thinnest piezoelectric layer and is constructed by n piezoelectric layers, for example, two piezoelectric layers electrically connected in series and laminated with the polarity directions of the adjacent piezoelectric layers set opposite to each other so as to make use of the resonance occurring at the resonant frequency ($f_0$) of the lowest order which can be obtained when piezoelectric layers of the same thickness are laminated and the resonance occurring at the resonant frequency of $f_0/n$ ($f_0/2$). As the result, the ultrasonic probe head can transmit/receive ultrasonic waves of two different frequency bandwidths.

The multilayer piezoelectric material of this invention can be formed with a three- or more-layered structure, but the multilayer piezoelectric material with two-layered structure is explained below only for simplicity. When the ratio R (=thickness of the piezoelectric layer on the radiation plane) of the thicknesses of the two piezoelectric layers having different thicknesses is changed, two excited resonant levels can be adjusted. Therefore, the ultrasonic probe of this invention can be applied in various fields by changing the ratio R according to the application thereof.

For example, when a to-be-tested object such as the heart which is located in a relatively deep position is observed from the body surface, the thickness ratio R is set to a small value to increase the resonance energy of the low frequency range in the bandwidth, that is, the frequency of $f_0$-2, thereby providing an ultrasonic probe which has a high sensitivity in the Doppler mode. In contrast, when a to-be-tested object such as the carotid artery and esophagus which are located in a relatively shallow position is observed, the thickness ratio R is set to a large value to increase the resonance energy of the high frequency range in the bandwidth, that is, the frequency of $f_0$, thereby providing an ultrasonic probe which has an extended high frequency range and can provide B mode images with high resolution in the B mode.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

Figure 1:
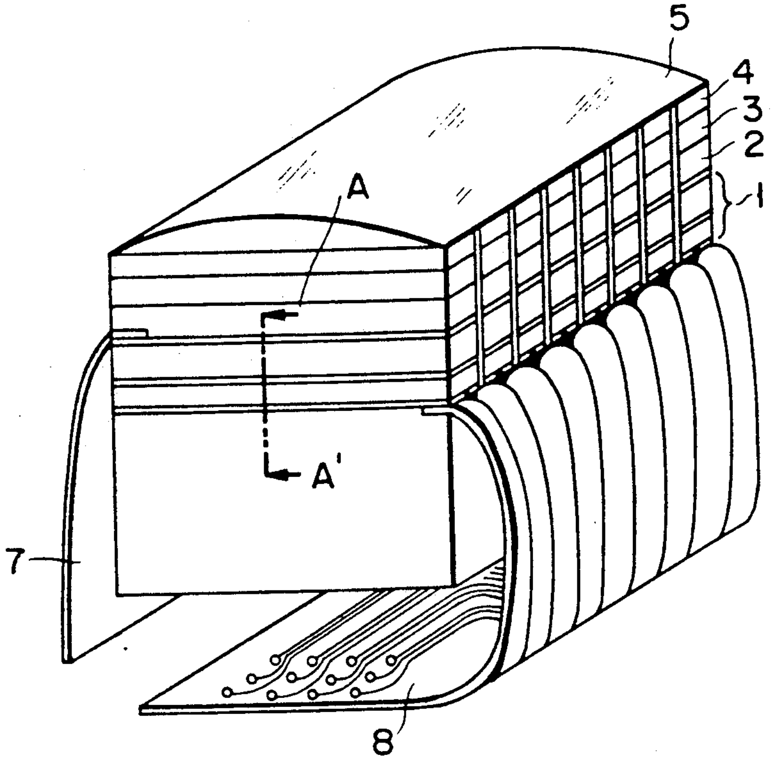
FIG. 1 is a perspective view showing the schematic construction of an ultrasonic probe (probe head) according to one embodiment of this invention.

FIG. 1 is a perspective view showing the schematic construction of the probe head of an ultrasonic probe according to one embodiment of this invention. In this embodiment, a multilayer piezoelectric material 1 is formed of a plurality of laminated piezoelectric elements. As shown in FIG. 1, a plurality of laminated acoustic matching layers 2 to 4 and an acoustic lens 5 are disposed on the ultrasonic wave radiation plane of the upper portion of the multilayer piezoelectric material 1, and a backing material 6 serving as a head backing plate is disposed on the rear side of the head lying on the opposite side of the radiation plane. The above elements are integrally laminated. Further, two external electrodes for power supply to the probe head are disposed. More specifically, an earth cable part of which serves as the external electrode and a lead line lead-out flexible print cable (FPC) board 8 on which a desired printed wiring pattern is formed are dispose don the outer surfaces of the upper and lower piezoelectric elements constituting the multilayer piezoelectric material 1.

Figure 2:
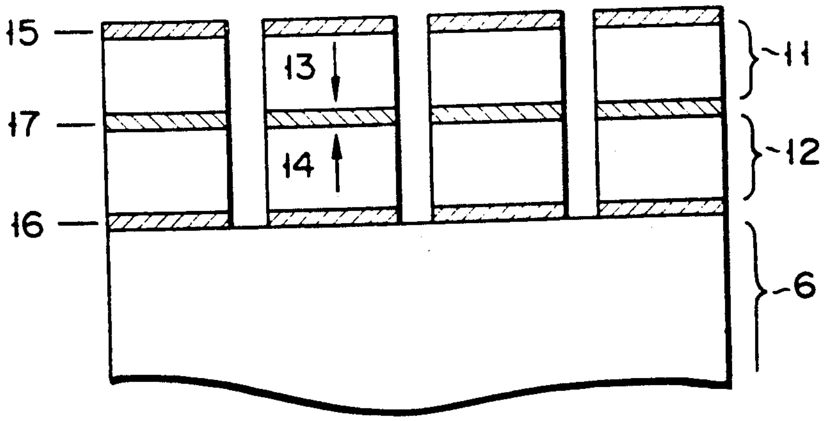
FIG. 2 is an enlarged cross sectional view of a two-layered multilayer piezoelectric material taken along the line A—A' of FIG. 1.

FIG. 2 is an enlarged cross sectional view of the multilayer piezoelectric material 1 taken along the line A—A' of FIG. 1. For example, piezoelectric layers 11 and 12 are laminated with the polarity directions 13 and 14 thereof set opposite to each other as shown in FIG. 2, and an internal electrode 17 is formed in the interface area between the two piezoelectric layer. External electrodes 15 and 16 are disposed on both end surfaces the multilayer piezoelectric material 1 in the laminated direction, that is, the upper side of the piezoelectric layer 11 and the lower side of the piezoelectric layer 12. Each of the piezoelectric layers 11 and 12 is formed of piezoelectric ceramic. The internal electrode 17 is formed to polarize the piezoelectric layers 11 and 12. It is preferable to set the thickness of each of the piezoelectric layers 11 and 12 less than 100 μm.

Assuming that the thickness of the piezoelectric layers 11 and 12 is set to $t_0$ in the ultrasonic probe with the above construction, the total thickness can be expressed by $2t_0$. Further, the basic resonant frequency $f_0$ of the multilayer piezoelectric material 1 can be expressed by $f_0 = v/2t_0$.

The basic resonant frequency of a single-layered piezoelectric layer having a thickness of $t_0$ can also be expressed by $v/2t_0$. This is because the polarity directions of the laminated piezoelectric layers 11 and 12 are opposite to each other and the piezoelectric layers 11 and 12 are electrically connected in series so that a resonance in which the total thickness $2t_0$ of the two piezoelectric layers is set equal to half the wavelength will not occur and a resonance in which the thickness $t_0$ of each of the piezoelectric layers is set equal to half the wavelength may occur. That is, the multilayer piezoelectric material 1 has a thickness twice that of the single-layered piezoelectric element, but the resonant frequency thereof is equal to that of the single-layered piezoelectric element, thus providing a piezoelectric element having the same frequency characteristic.

Therefore, with the multilayer piezoelectric material 1, the total thickness can be increased in comparison with the single-layered piezoelectric element so that deterioration in the characteristic caused in the sintering process or at the time of forming the electrodes 15 and 16 can be suppressed to minimum, the workability can be enhanced and occurrence of damages can be suppressed to minimum.

For example, the piezoelectric layers 11 and 12 are formed of PZT-series ceramic with the dielectric constant of 2000 and the thickness of each piezoelectric layer is set to 75 μm. The piezoelectric layer is used as a plurality of transducer elements which are cut into a strip form and adequately arranged. In this example, the measurement of $k'_{33}$ wad 64%. For example, in manufacturing the probe head of the ultrasonic probe shown in FIG. 1, acoustic matching layers 2 to 4 with a predetermined thickness are disposed o the ultrasonic wave radiation plane of the multilayer piezoelectric material 1, the earth cable 7 is bonded between the acoustic matching layer and the electrode 15 by soldering, for example, and the lead line lead-out FPC board 8 is bonded between the electrode 16 and the backing material 6 by soldering, for example. After this, the plate of the multilayer piezoelectric material is cut into the strip form as shown in FIG. 2 by a dicing machine. In this cutting operation, a blade with a thickness of 15 μm is used and the cutting pitch is set to 60 μm. The number of strip-form transducers thus formed is 64. When the pulse echo characteristic of the transducers was measured, it was determined that the central frequency was 19.8 MHz at the time of operating all the transducers.

An ultrasonic probe using a single-layered piezoelectric element with a thickness of 75 μm was formed as a comparison example. The measured value of $k'_{33}$ of the single-layered piezoelectric element was 56% which is less than that of this invention by 9%. Further, warp occurred in the single-layered piezoelectric element and 10% of the single-layered piezoelectric elements used were damaged at the time of soldering the flexible print board and the earth cable together. It was also determined that 8% of the single-layered piezoelectric elements were damaged at the time of bonding the same to the backing material 4 and thus it was clearly confirmed that the manufacturing yield of the single-layered piezoelectric element was lowered.

When the echo waveforms were obtained by effecting the pulse echo method for the embodiment of this invention and the comparison example and were compared with each other, the measurement of the latter case was −3 dB and thus exhibited low sensitivity.

Figure 3:
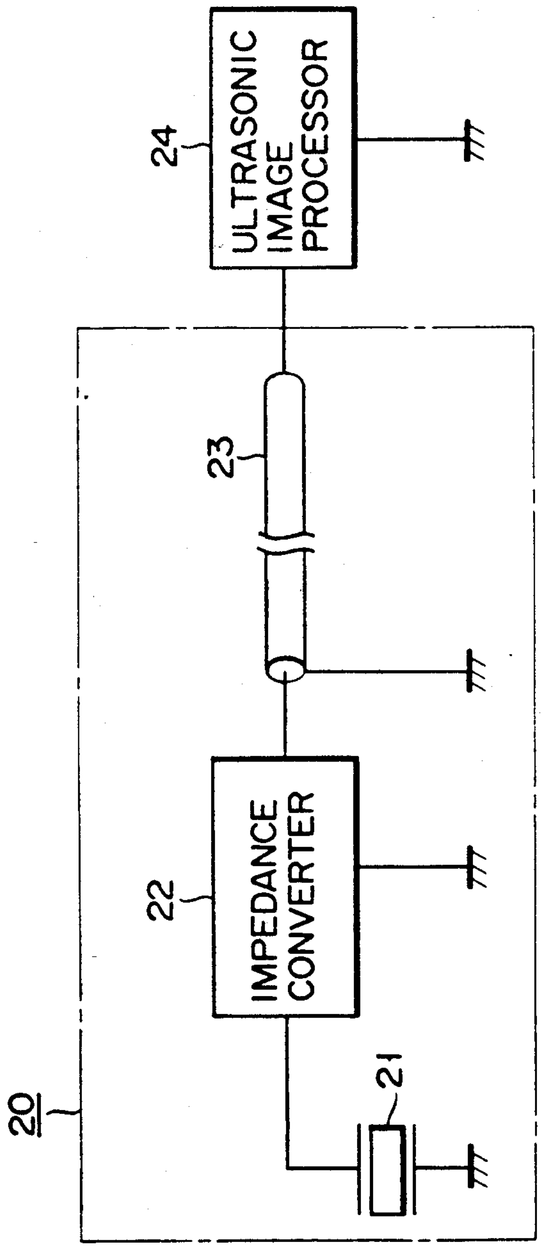
FIG. 3 is a schematic diagram showing an equivalent construction of an ultrasonic probe according to a second embodiment of this invention.

FIG. 3 is a schematic diagram showing an equivalent construction of an ultrasonic probe according to a second embodiment of this invention. As shown in FIG. 3, the ultrasonic probe body 21 is formed of an ultrasonic probe head constructed in the same manner as the ultrasonic probe shown in FIGS. 1 and 2. That is, an impedance transducer 22 is inserted between the electrode 15 of the ultrasonic probe body 21 and one end of a coaxial cable 23. The impedance transducer 22 is constituted by using an emitter follower circuit including a bipolar transistor, for example, and the input terminal thereof is connected to the external electrode 15 (refer to FIG. 2) and the output terminal is connected to one end of the coaxial cable 23. The other end of the coaxial cable 23 is connected to an input terminal (receiving section) of the ultrasonic diagnostic apparatus 24. In practice, since the ultrasonic probe body 21 is formed of a large number of transducer elements, the same number of impedance transducers 22 and coaxial cables 23 as that of the transducer elements are provided.

In the ultrasonic probe body (probe head) 21, the piezoelectric layers 11 and 12 are electrically connected in series in the same manner as shown in FIGS. 1 and 2. Therefore, the electrostatic capacitance between the electrodes 15 and 16 of the multilayer piezoelectric material 1 is reduced and the impedance is increased. As a result, when the ultrasonic probe body 21 ia connected directly to the coaxial cable 23, the voltage loss due to the presence of the electrostatic capacitance of the coaxial cable 23 increases, but the voltage loss can be reduced by inserting the impedance transducer 22 between the ultrasonic probe body 21 and the coaxial cable 23 to lower the effective impedance of the ultrasonic probe.

Further, according to this embodiment, when the same electric power as in the case of the single-layered piezoelectric element is supplied to piezoelectric layers 11 and 12 in the ultrasonic probe body 1, that is, when the driving voltage is increased to $\sqrt{2}$ times the driving voltage set in the single-layered piezoelectric element to set the amount of generated heat to the same value, then the electric field is decreased to $1/\sqrt{2}$ times that set in the single-layered piezoelectric element. As a result, the sound pressure of the ultrasonic waves caused by the first expansion or contraction and radiated from one end face (for example, the surface of the piezoelectric layer 11) of the multilayer piezoelectric material 1 is reduced by $1/\sqrt{2}$ obtained in the case of the single-layered piezoelectric element. However, the second and succeeding ultrasonic waves are a combination of waves propagated from the other end face (for example, the rear surface of the piezoelectric layer 12) of the multilayer piezoelectric material 1 and waves caused by reflection of the above waves at the end faces of the multilayer piezoelectric material 1. In the case of the two-layered multilayer piezoelectric material shown in FIG. 2, since the total thickness of the piezoelectric layer is twice that of the single-layered piezoelectric element, the amplitude of the ultrasonic waves for particularly the third waves is increased by an amount corresponding to the reduced number of reflections of the ultrasonic waves at the end face in comparison with the case of the single-layered piezoelectric element. Further, assuming that the ultrasonic waves of the same sound pressure are received in the reception mode, then the electric field which is obtained in the two-layered multilayer piezoelectric material 1 shown in FIG. 2 becomes one half that obtained in the case of the single-layered piezoelectric element, and in this case, since the total thickness of the former is twice that of the latter, voltage generated by the first-received ultrasonic waves is set to a constant value irrespective of the number of layers. The generation voltage with respect to the second an succeeding ultrasonic waves is higher in the multilayer piezoelectric material than in the single-layered piezoelectric element.

As described above, according to this embodiment, the sound pressure of the ultrasonic wave i the transmission mode is increased and the generation voltage in the reception mode is also increased. Thus, the sensitivity can be improved in the transmission and reception modes, thereby enhancing the total performance of the ultrasonic probe. As the actual result, the level of the echo signal supplied from the to-be-tested body and detected on the reception side becomes high.

As a concrete example, the two-layered multilayer piezoelectric material 1 shown in FIGS. 1 and 2 was used in the ultrasonic probe body 21, and the thickness of the piezoelectric layers 11 and 12 is set to approx. 400 ρm. As was explained in the former embodiment, in manufacturing the probe body 21, a dicing machine having a blade of 50 μm thickness was used to cut apart the multilayer piezoelectric material at a pitch of 250 μm, thus constructing the transducer section by 64 elements.

At the same time, an ultrasonic probe having a single-layered piezoelectric element with a thickness of 400 μm was formed as a comparison example.

The pulse echo characteristics for heat generation in the piezoelectric layer of the above embodiments and the above comparison example were measured under the same condition. The result showed that the peak value was higher by approx. 3 dB in the above embodiments than in the comparison example.

In the above embodiments, the two-layered multilayer piezoelectric material is mainly explained, but three- or more-layered multilayer piezoelectric material can be used.

Figure 4:
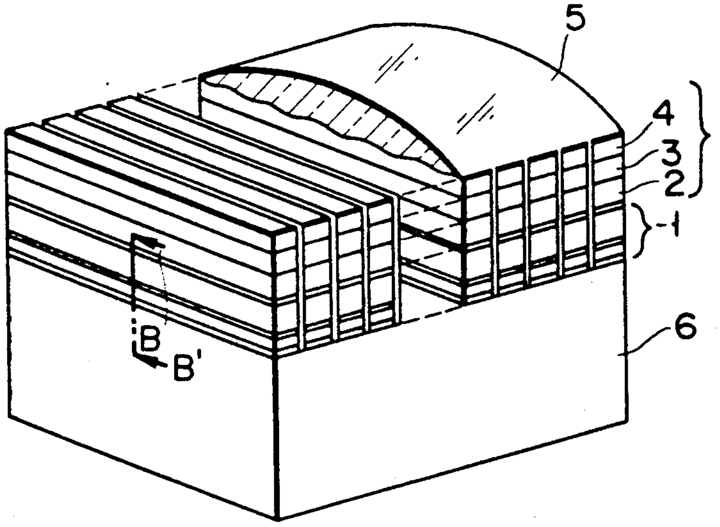
FIG. 4 is a perspective view showing the schematic construction of a probe head of the ultrasonic probe according to a third embodiment of this invention.

FIG. 4 is a perspective view showing the schematic construction of an ultrasonic probe head according to a third embodiment of this invention. As shown in FIG. 4, a plurality of laminated acoustic matching layers 2 to 4 and an acoustic lens 5 serving as a radiation plane are disposed on the ultrasonic wave radiation plane of the upper portion of the multilayer piezoelectric material 1, and a backing material 6 serving as a substrate is disposed on the rear side of the head lying on the opposite side of the radiation plane. The feature of this embodiment lies in a difference in the thicknesses of a plurality of constituting the multilayer piezoelectric layers shown in FIG. 5.

Figure 5:
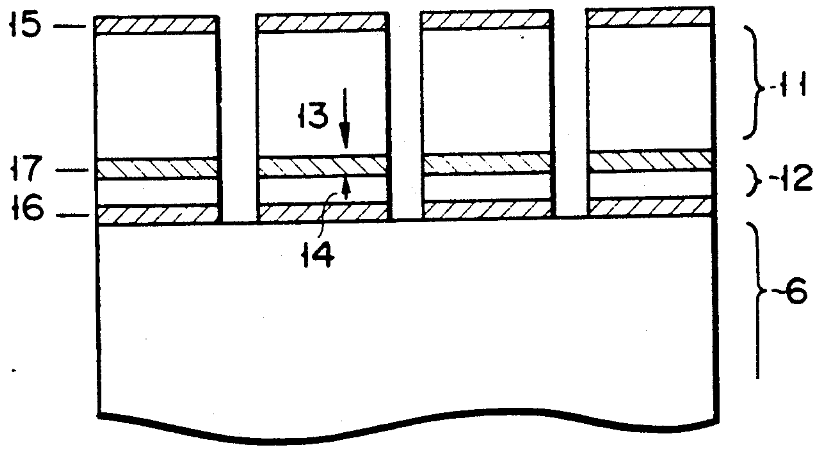
FIG. 5 is an enlarged cross sectional view of a two-layered multilayer piezoelectric material taken along the line B—B' of FIG. 4.

FIG. 5 is an enlarged cross sectional view of a two-layered multilayer piezoelectric material taken along the line B—B' of FIG. 4. As shown in FIG. 5, the multilayer piezoelectric material 1 has two piezoelectric layers 11 and 12 laminated with the polarity directions 13 and 14 thereof set opposite to each other. External electrodes 15 and 16 are formed on the respective end faces of the multilayer piezoelectric material in the laminated direction, that is, on the upper surface of the piezoelectric layer 11 and on the lower surface of the piezoelectric layer 12. Each of the piezoelectric layers 11 and 12 is formed of piezoelectric ceramic. In practice, an internal electrode 17 used for polarizing the piezoelectric layers 11 and 12 is disposed between the piezoelectric layers 11 and 12. As a concrete example, the piezoelectric layers 11 and 12 are formed of PZT-series ceramic with the dielectric constant of 2000, the thickness of the piezoelectric layer 11 is set to 260 μm, the thickness of the piezoelectric layer 12 is set to 180 μm, and thus the thickness ratio R of the two piezoelectric layers 11 and 12 is set to approx. 0.7. That is, the piezoelectric layer 12 which is far apart from the acoustic lens 5 on the ultrasonic wave radiation plane and is adjacent to the backing material 6 serving as the substrate is formed thinner than the piezoelectric layer 11.

The thicknesses of the three-layered acoustic matching layers 2 to 4 are so determined as to attain the frequency matching in the high frequency range. This is because the frequency characteristic is set to have a wide bandwidth to attain a B mode signal in the high frequency range.

With the above ultrasonic probe, an earth common electrode (not shown) and signal flexible print board (not shown) are respectively bonded by soldering to the electrodes 15 and 16, and a blade with a thickness of 30 μm is cut off together with the acoustic matching layers 2 to 4 by means of a dicing machine in accordance with the signal line pitch (0.15 mm) of the flexible print board.

Figure 6:
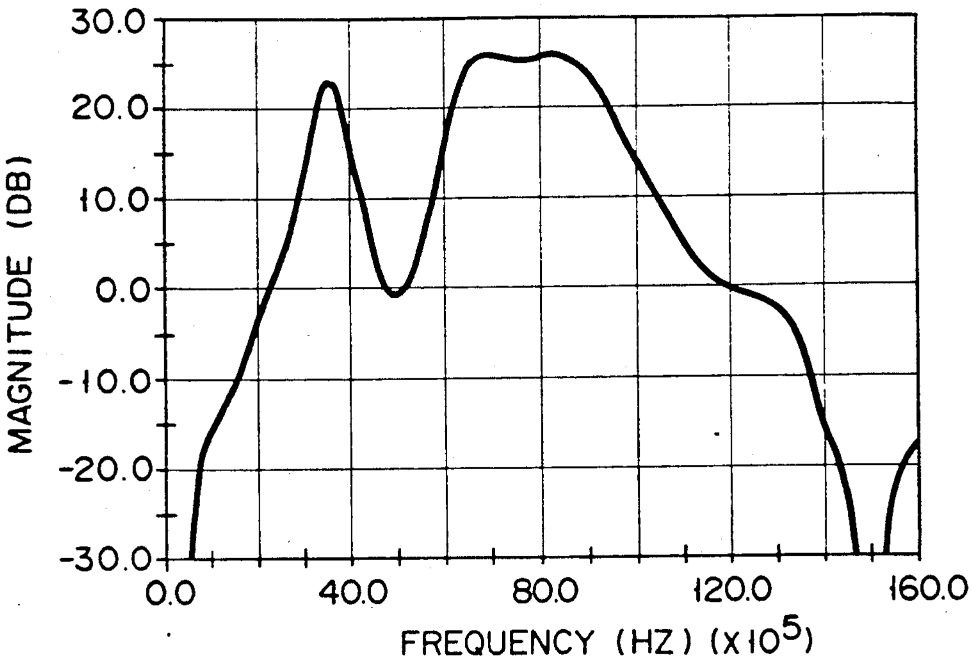
FIGS. 6 and 7 are graphs showing frequency spectra in the form of echo wave obtained by the pulse echo method.

FIG. 6 is a graph showing the frequency spectrum of an echo waveform reflected from a reflection plate disposed in water and measured by the "pulse echo method". As is clearly seen from the frequency spectrum curve in the graph, the central frequency of the convex portion of the high frequency range is about 7.76 MHz and the specific bandwidth is 43.2% which is a sufficiently large value to obtain B mode images. In this case, the central frequency of the convex portion of the low frequency range is about 3.51 MHz.

Figure 7:
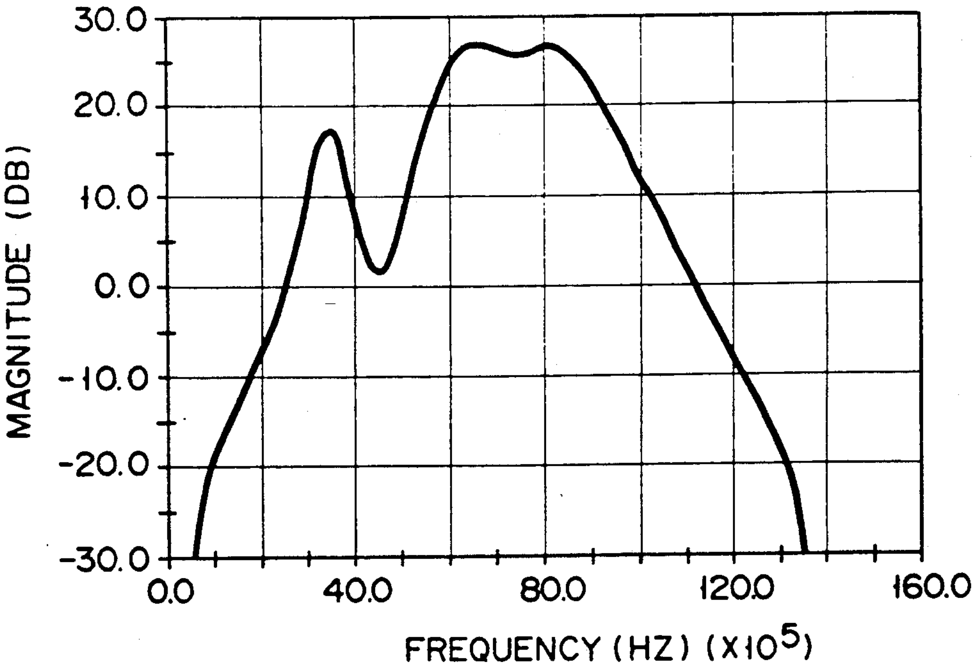

A graph of the frequency spectrum shown in FIG. 7 represents the measurement result obtained in the case of the third embodiment for the above results. That is, it is understood from FIG. 7 that, in the frequency spectrum obtained in the case of an ultrasonic probe in which the thickness of the piezoelectric layer 11 is set to 230 μm, the thickness of the piezoelectric layer 12 is set to 210 μm (R=0.91), and the other conditions are kept unchanged, then the central frequency on the high frequency side is 7.54 MHz and the specific bandwidth is 47.2%. From this, it is clearly understood that a wider bandwidth can be obtained in the third embodiment in comparison with the second embodiment.

It is possible to selectively use the ultrasonic probes for to-be-tested objects according to the characteristics thereof, for example, the ultrasonic probe of the first embodiment can be used for examining the esophagus and the ultrasonic probe of the second embodiment can be used for examining the heart from the body surface.

In the above embodiments, the two-layered multilayer piezoelectric material is mainly explained as an example, but this invention is not limited only to those embodiments and various modifications can be made without departing from the technical scope thereof. For example, it is possible to use a three- or more-layered multilayer piezoelectric material as the piezoelectric element.

As described above, according to this invention, an ultrasonic probe which has the following effects can be obtained. That is, the basic resonant frequency can be enhanced to approx. 15 to 30 MHz without lowering the manufacturing yield by forming the ultrasonic probe by use of a multilayer piezoelectric material having a plurality of laminated piezoelectric layers which are electrically connected in series via electrodes formed on both end faces thereof. Further, high sensitivity can be attained by inserting the impedance transducer constituted by an emitter follower circuit or the like between the electrode and the coaxial cable to lower the impedance of the ultrasonic probe.

Further, according to this invention, it becomes possible to transmit/receive waves of a plurality of different frequencies, for example, two different frequencies by using an ultrasonic probe which includes a multilayer piezoelectric material in which a piezoelectric layer located farthest away from the ultrasonic wave radiation plane is formed to have the smallest thickness. In addition, the specific bandwidth of the high frequency region can be adequately adjusted according to the application field of the ultrasonic probe by adequately changing the thickness ratio of the piezoelectric layers of the multilayer piezoelectric material.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An ultrasonic probe comprising:

a piezoelectric element having a plurality of piezoelectric layers laminated in a thickness direction with the polarized directions of the adjacent piezoelectric layers set opposite to each other and each having opposite end faces; and electrodes formed on said opposite end faces of said piezoelectric layers in the laminated direction wherein the thickness of one of said plurality of piezoelectric layers which is located in an endmost position is set to a smallest value in comparison with that of the other adjacent piezoelectric layers.

2. An ultrasonic probe according to claim 1, further comprising:

head backing means formed on a first surface of said piezoelectric element;

ultrasonic frequency matching means formed on a second surface opposed to said first surface of said piezoelectric element; and ultrasonic wave converging means formed on said ultrasonic frequency matching means.

3. An ultrasonic probe according to claim 2, wherein said head backing means is a backing material, said ultrasonic frequency matching means is an acoustic matching layer and said ultrasonic wave converging means is an acoustic lens.

4. An ultrasonic probe according to claim 1, wherein said piezoelectric layer is formed of piezoelectric ceramic and the thickness of said piezoelectric layer is set less than 100 μm.

5. An ultrasonic probe according to claim 1, further comprising:

head backing means disposed on one surface of said piezoelectric element;

ultrasonic frequency matching means disposed on the other surface of said piezoelectric element; and ultrasonic wave converging means disposed on said ultrasonic frequency matching means; and wherein said piezoelectric element includes a piezoelectric layer which is one of said plurality of piezoelectric layers and is located farthest away from said ultrasonic wave converging means and adjacent to said head backing means dispose don said one surface of said piezoelectric element and whose thickness is set to a smallest value in comparison with that of the other piezoelectric layers and said head backing means, said ultrasonic frequency matching means and said ultrasonic wave converting means are combined to constitute probe head means.

6. An ultrasonic probe according to claim 5, wherein said head backing means is a backing material and said ultrasonic frequency matching means is an acoustic matching layer.

7. An ultrasonic probe according to claim 1, wherein said piezoelectric element is constructed by two piezoelectric layers which are formed of a PZT-series ceramic.

8. An ultrasonic probe comprising:

ultrasonic wave transmitting/receiving head means having:

a piezoelectric element including a plurality of piezoelectric layers laminated in a thickness direction with the polarized directions of the adjacent piezoelectric layers set opposite to each other and each having opposite end faces, a first electrode formed on said opposite end faces of said plurality of piezoelectric layers in the laminated direction, and wherein a thickness of one of said plurality of piezoelectric layers which is locate din an endmost position is set to a smallest value in comparison with that of the other adjacent piezoelectric layers;

ultrasonic frequency matching means including a plurality of layers and formed on a first surface of said plurality of laminated piezoelectric layers;

ultrasonic wave converging means formed on said ultrasonic frequency matching means with the convex surface thereof set towards the outside; and head backing means formed on a second surface opposed to said first surface.

9. An ultrasonic probe according to claim 8, further comprising:

grounding means connected to one surface of a layer formed of said plurality of electrodes; and printed wiring means having a printed wiring pattern which is connected to the other surface of said layer of said plurality of electrodes.

10. An ultrasonic probe according to claim 8, wherein said probe head means further comprises:

grounding means connected between said electrodes and said acoustic matching layer which is formed on the ultrasonic wave radiation side of said piezoelectric element with a predetermined thickness by soldering; and printed wiring means connected between said electrodes and said head backing means by soldering.

11. An ultrasonic probe according to claim 10, wherein said first electrode is an external electrode; said second electrode is an internal electrode; said head backing means is a backing material; said ultrasonic frequency matching means is an acoustic matching layer; said ultrasonic wave converging means is an acoustic lens; said grounding means is an earth cable, and said printed wiring means is a flexible print cable.

* * * * *